United States Patent
Lin

[19]

[11] Patent Number: 5,820,792
[45] Date of Patent: Oct. 13, 1998

[54] PERFUME DISPENSER

[76] Inventor: Hsi Huang Lin, P. O. Box 82-144, Taipei, Taiwan

[21] Appl. No.: 804,758

[22] Filed: Feb. 24, 1997

[51] Int. Cl.$^6$ ........................................................ B01F 3/04
[52] U.S. Cl. ...................... 261/30; 261/35; 261/DIG. 65; 422/124
[58] Field of Search ............................... 261/30, DIG. 65, 261/35; 422/124

[56] References Cited

U.S. PATENT DOCUMENTS

| | | | |
|---|---|---|---|
| 2,083,607 | 6/1937 | Joseph | 261/30 |
| 2,867,866 | 1/1959 | Steele | 422/124 |
| 4,523,870 | 6/1985 | Spector | 261/DIG. 65 |
| 4,654,198 | 3/1987 | Berardini | 422/124 |
| 4,840,773 | 6/1989 | Wade | 422/124 |
| 5,269,723 | 12/1993 | Bender | 422/124 |
| 5,478,505 | 12/1995 | McElfresh et al. | 261/DIG. 65 |

*Primary Examiner*—Tim R. Miles
*Attorney, Agent, or Firm*—A & J

[57] ABSTRACT

A perfume dispenser includes a housing, a fan and a perfume respectively mounted in the housing at different elevations and separated by a partition wall, the housing having clamping plates for mounting in louvers of an air output port of an air conditioner, a first air inlet adapted for guiding currents of air from the air conditioner into the fan chamber to turn the fan, a second air inlet adapted for guiding outside air into the perfume chamber, and a plurality of air outlets adapted for guiding air out of the fan chamber, the partition wall defining an air passage through which air passes from the perfume chamber to the fan chamber.

4 Claims, 3 Drawing Sheets

PERFUME DISPENSER

BACKGROUND OF THE INVENTION

1. Field of the Invention

This invention relates to a perfume dispenser, and more particularly to such a perfume dispenser adapted for hanging on louvers of an air output port of an air conditioner to utilize the output currents of air from the air conditioner for dispensing a perfume into the air.

2. Description of the Prior Art

A variety of perfume dispensers have been disclosed for use in offices, houses, motor vehicles, etc., for dispensing a perfume, and have appeared on the market. These perfume dispensers are commonly comprised of a perfume container having air vents, and a solid or liquid perfume contained in the perfume container. These perfume dispensers are less active, and the smell of the perfume used cannot be quickly and effectively distributed into the air.

SUMMARY OF THE INVENTION

This invention provides a perfume dispenser which utilizes the output currents of air of an air conditioner to dispense a perfume. According to the present invention, the perfume dispenser comprises a casing, the casing comprising a partition plate, a fan chamber and a perfume chamber separated by the partition plate of the casing, a plurality of air outlets in communication with the fan chamber, and a plurality of retaining holes, the partition plate of the casing having a semi-circular notch; a cover covered on the casing, the cover comprising a partition plate horizontally abutted against the partition plate of the casing and having a semi-circular notch matched with the semi-circular notch of the partition plate of the casing into a circular hole through which air passes from the perfume chamber into the fan chamber, an air inlet through which air passes from the outside toward the air outlets through the fan chamber, a plurality of hooks respectively hooked in the retaining holes of the casing, and a bottom hole adapted for guiding outside air into the perfume chamber; a fan mounted in the fan chamber and turned by currents of air input from the air inlet to draw currents of air from the perfume chamber into the fan chamber and then to drive currents of air out of the fan chamber through the air outlets; and a perfume mounted inside the perfume chamber. The cover further comprises clamping plates at the back side adapted for fastening to louvers of an air output port of an air conditioner, so that output currents of air from the air conditioner can be guided into the fan chamber to turn the fan.

DETAILED DESCRIPTION OF THE PREFERRED EMBODIMENT

Figure 1:
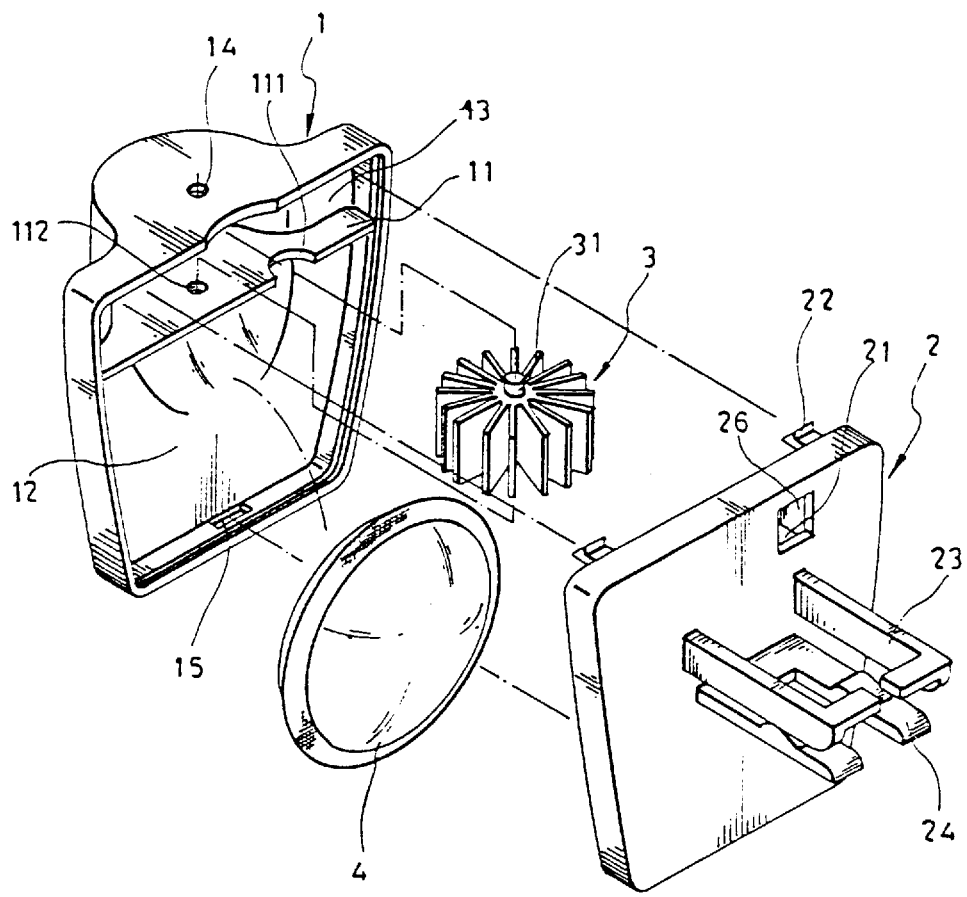
FIG. 1 is an exploded view of a perfume dispenser according to the present invention.
Figure 2:
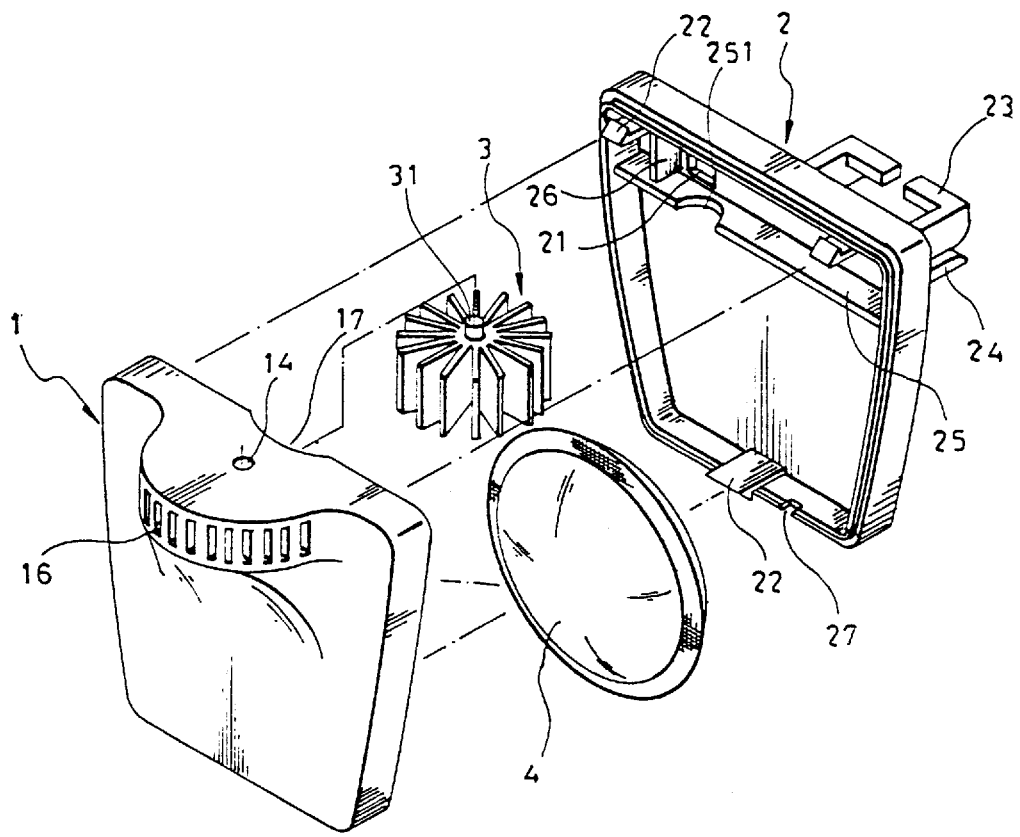
FIG. 2 is another exploded view of the perfume dispenser of the present invention when viewed from another angle.

Referring to FIGS. 1 and 2, a perfume dispenser in accordance with the present invention is generally comprised of a casing 1, a cover 2, a fan 3, and a perfume 4.

Figure 3:
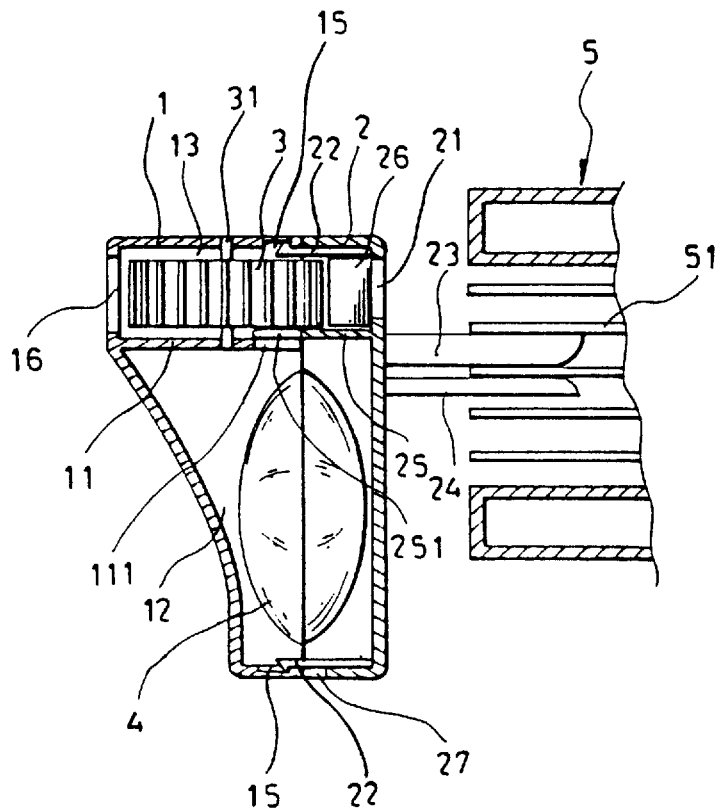
FIG. 3 is a sectional assembly view of the present invention, showing the perfume dispenser installed.

Referring to FIG. 3 and FIGS. 1 and 2 again, the casing 1 comprises a partition plate 11 defining a perfume chamber 12 and a fan chamber 13, a plurality of air outlets 16 arranged in a horizontally disposed smoothly curved line and disposed in communication with the fan chamber 13, a first pivot hole 14 at the top side thereof, a second pivot hole 112 at the partition plate 11, a semi-circular notch 111 at the border of the partition plate 11, a top notch 17, and a plurality of retaining holes 15 on the inside.

The fan 3 is mounted within the fan chamber 13, having a fan shaft 31 pivotably coupled to the first pivot hole 14 and the second pivot hole 112.

The cover 2 is covered on the casing 1, comprising a partition plate 25 horizontally abutted against the partition plate 11 of the casing 1, a semi-circular notch 251 disposed at the partition plate 25 and matched with the semi-circular notch 111 of the casing 1, an air inlet 21 adjacent to the semi-circular notch 251, a wind guide 26 at one side of the air inlet 21 for guiding intake flow of air toward the air outlets 16 through the fan 3, a plurality of hooks 22 respectively hooked in the retaining holes 15 of the casing 1, a bottom hole 27, and two backward clamping plates 23; 24 perpendicularly raised from the back side.

The perfume 4 is mounted within the perfume chamber 12 of the casing 1.

Referring to FIG. 3, when the fan 3 and the perfume 4 are respectively mounted in the fan chamber 13 and perfume chamber 12 of the casing 1, the cover 2 is covered on the casing 1, and then the clamping plates 23; 24 are fastened to louvers 51 of an air output port 5 of an air conditioner. When the air conditioner is operated, currents of air flow from the air output port 5 into the air inlet 21, and are guided by the wind guide 26 to pass through the periphery of fan 3, causing the fan 3 to be rotated. When the fan 3 is rotated, an upward flow of air is induced into the casing 1 from the bottom hole 27 of the cover 2. At the same time, the smell of the perfume 4 is carried by the induced upward flow of air from the perfume chamber 12 into the fan chamber 11 through the circular hole, which is formed of the semi-circular notches 111; 251, and then driven out of the air outlets 16 by the fan 3. Further, the total area of the air outlets 16 is greater than the area of the air inlet 21, so that intake currents of air passing through the air inlet 21 can be fully driven out of the air outlets 16. While only one embodiment of the present invention has been shown and described, it will be understood that various modifications and changes could be made thereunto without departing from the spirit and scope of the invention disclosed.

I claim:

1. A perfume dispenser comprising:

a casing, said casing comprising a partition plate, a fan chamber and a perfume chamber separated by the partition plate of said casing, a plurality of air outlets in communication with said fan chamber, and a plurality of retaining holes, the partition plate of said casing having a semi-circular notch;

a cover covered on said casing, said cover comprising a partition plate horizontally abutted against the partition plate of said casing and having a semi-circular notch matched with the semi-circular notch of the partition plate of said casing into a circular hole through which air passes from said perfume chamber into said fan chamber, an air inlet through which air passes from the outside toward said air outlets through said fan chamber, a plurality of hooks respectively hooked in the retaining holes of said casing, and a bottom hole adapted for guiding outside air into said perfume chamber;

a fan mounted in said fan chamber and turned by currents of air inputted from said air inlet to draw currents of air from said perfume chamber into said fan chamber and then to drive currents of air out of said fan chamber through said air outlets; and a perfume mounted inside said perfume chamber.

2. The perfume dispenser as claimed in claim 1, wherein said cover further comprises a wind guide adapted for guiding currents of air from said air inlet through the periphery of said fan.

3. The perfume dispenser as claimed in claim 1, wherein said cover comprises mounting means adapted for fastening to louvers of an air output port of an air conditioner.

4. The perfume dispenser as claimed in claim 3, wherein said mounting means comprises a pair of clamping plates perpendicularly raised from said cover at a back side thereof.

* * * * *